United States Patent [19]

Goss

[11] Patent Number: 5,702,714

[45] Date of Patent: Dec. 30, 1997

[54] SKIN CONDITIONER

[76] Inventor: Louis Goss, 3007 Windy Knoll Ct., Rockville, Md. 20850

[21] Appl. No.: 627,056

[22] Filed: Apr. 3, 1996

Related U.S. Application Data

[63] Continuation-in-part of Ser. No. 478,353, Jun. 7, 1995, abandoned.

[51] Int. Cl.⁶ ..................................................... A61K 7/48
[52] U.S. Cl. ........................................... 424/401; 514/844
[58] Field of Search ............................ 424/401; 514/844

[56] References Cited

U.S. PATENT DOCUMENTS 5,525,344   6/1996   Wivell ..................................... 424/401

*Primary Examiner*—Jyothsna Venkat
*Attorney, Agent, or Firm*—Patrick J. Walsh

[57] ABSTRACT

A skin conditioner composition comprising: di alpha tocopherol liquid, PCL wax or solid, PCL oil, fumed silica, squalane decyl oleate, squalane liquid, wheat germ glyceride, Proto-Lan 8, ppg-26 oleate, perfume, p-hydroxy benzyl benzoate, guaiazulene.

3 Claims, No Drawings

SKIN CONDITIONER

This application is a continuation-in-part of application Ser. No. 08/478,353 filed Jun. 7, 1995, now abandoned.

BACKGROUND OF THE INVENTION

The present invention relates to a composition for conditioning skin.

SUMMARY OF THE INVENTION

The present invention comprises a composition with the properties of softening skin, with unique rejuvenating characteristics. A composition blended according to the invention improves skin condition by rejuvinating the skin, soothing skin redness, feeding the skin, smoothing wrinkles, and providing a shine to the skin without greasiness. The composition is absorbed into the skin and cannot be washed off except by use of soap and water.

A composition in accordance with the invention, includes di alpha tocopherol liquid, PCL wax or solid, PCL oil, fumed silica, squalane decyl oleate, squalane liquid, wheat germ glyceride, Proto-Lan 8, ppg-26 oleate, perfume, p-hydroxy benzyl benzoate, guaiazulene.

OBJECTS OF THE INVENTION

It is an object of the invention to provide a skin conditioner.

It is an object of the invention to provide a composition for treating skin to achieve healing, soothe redness, feed the skin, puff up wrinkles, be absorbrd in the skin, and to give the skin a shine without greasiness.

It is a further object of the invention to provide a composition comprising specific ingredients for conditioning the skin.

Other and further objects of the invention will occur to one skilled in the art with an understanding of the following detailed description of the invention or upon employment of the invention in practice.

DETAILED DESCRIPTION OF THE INVENTION

A composition in accordance with invention includes the following components.

Di alpha tocopherol liquid, an oil soluble, viscous oil stable to light, heat and air, and which possesses anti-oxident properties, i.e., prevents many natural components in the skin and body from becoming oxidized. Di alpha tocopherol liquid is a vitamin E oil, is clear, yellow to greenish-yellow or nearly colorless, is the most biologically active of all tocopherols, and is the major lipid-soluble anti-oxident responsible for protecting the poly-unsaturated fatty acids in the skin and body against lipid peroxidation. Di alpha tocopherol is a skin moisturized and softener.

PCL (purcellin) wax or solid is a waxy fat, consisting of long chain fatty acid esters, is soluble in oils only, is a viscosity increasing component exhibiting pronounced hydrophobic properties. PCL wax or solid improves skin texture.

PCL (purcellin) oil (cetearyl octanoate), is a liquid fat consisting of a mixture of branched alkyd-fatty-acid esters soluble in oils only. PCL oil is a good film former, has excellent spreading capacity, improves natural water vapor permeability of the skin, and makes the skin soft, smooth and supple.

Fumed silica is a high purity silica which provides viscosity control and reinforcement, and has the ability to absorb one-third its weight in oil. Fumed silica is a gelling agent for oil and a film former when applied to the skin to prevent moisture escape and maintain skin moisture while retaining oils in contact with the skin.

Decyl oleate is an ester which is soluble and blends with oils and fatty raw materials. Decyl oleate provides emolliency and improves skin softness and feel.

Squalane liquid (known by the tradename Robane) is a saturated aliphatic hydrocarbon appearing as a colorless, transparent odorless oil, and occurs in the sabaceous glands of the skin. Squalane is non-toxic, non-irritating, hypoallergenic and non-sensitizing when in contact with the skin. Squalane occurs naturally in the skin and prevents volatilization of moisture from the skin thus providing a moisturizing effect. Squalane imparts suppleness to the skin without a greasy feel.

Wheat germ glyceride appears as a straw-yellow, semisolid oil, and is an effective skin lubricant, emollient and skin softener. Wheat germ glyceride aids in reducing skin irritation of other topical ingredients. It is known by the trade name Wickenol 535.

Proto-Lan 8 is a trade name for a combination of lecithin, butyl stearate, cocoyl hydrolyzed collagen, oleyl sarcosine, sesame oil and lanolin alcohol. Proto-Lan 8 is a non-greasy, non-tacky, oil soluble emollient based on naturally occurring phospho-lipids complexed with lipo-poly peptides and lipo-amino acids. Proto-Lan 8 is rapidly absorbed by the skin and provides relief from dry chapped skin while providing long lasting moisturization.

Ppg-26 oleate (polyoxy propylene ester) is an oil soluble, non-greasy, non-tacky, non-staining oil and serves as a spreading skin emollient and as a carrier or dispersant for vitamins, moisturizers, lanolin deravitives and essential oils.

Perfume is a hypo-allergenic oil soluble liquid combination to provide an acceptable odor to the composition and to mask any unwanted or unnecessary odors.

P-hydroxy benzyl benzoate is an oil soluble white powder serving as a perservative against bacterial and mold growths in oily products.

Guaiazulene (azulene 100%, 1,4-dimethyl-7-isopropyl-azulene) is an extract of the camomile plant and exhibits anti-infammatory in oral and skin products and imparets a natural blue color to the final product.

A preferred composition according to the invention includes an effective amount of each ingredient selected from the following range of percentages by weight of the active ingredients:

| ITEM | PERCENTAGE |
| --- | --- |
| Di alpha tocopherol | 0.5–94.5 |
| PCL wax or solid | 0.5–94.5 |
| PCL (purcellin) oil (cetearyl octanoate) | 0.5–94.5 |
| Fumed silica | 0.5–94.5 |
| Decyl oleate | 0.5–94.5 |
| Squalane | 0.5–94.5 |
| Wheat germ glyceride | 0.5–94.5 |
| Proto-Lan 8 | 0.5–94.5 |
| Ppg-26 oleate (polyoxy propylene ester) | 0.5–94.5 |
| Perfume | 0.5–94.5 |
| P-hydroxy benzyl benzoate | 0.5–94.5 |
| Guaiazulene (azulene 100%, 1,4-dimethyl-7-isopropyl-azulene) | 0.5–94.5 |

A composition according to the invention includes the following range of percentages by weight of the active ingredients:

| ITEM | PERCENTAGE |
|---|---|
| Di alpha tocopherol | 45–55 |
| PCL wax or solid | 14–18 |
| PCL (purcellin) oil (cetearyl octanoate) | 7–9 |
| Fumed silica | 6–8 |
| Decyl oleate | 4–6 |
| Squalane | 4–6 |
| Wheat germ glyceride | 3–4 |
| Proto-Lan 8 | 3–4 |
| Ppg-26 oleate (polyoxy propylene ester) | 1–3 |
| Perfume | 0.20 |
| P-hydroxy benzyl benzoate | 0.18 |
| Guaiazulene (azulene 100%, 1,4-dimethyl-7-isopropyl-azulene) | 0.02 |

A preferred composition according to the invention has the following ingredients in percentage by weight.

| ITEM | PERCENTAGE |
|---|---|
| Di alpha tocopherol | 50.00 |
| PCL wax or solid | 16.00 |
| PCL (purcellin) oil (cetearyl octanoate) | 8.00 |
| Fumed silica | 7.00 |
| Decyl oleate | 5.00 |
| Squalane | 5.00 |
| Wheat germ glyceride | 3.60 |
| Proto-Lan 8 | 3.00 |
| Ppg-26 oleate (polyoxy propelene ester) | 2.00 |
| Perfume | 0.20 |
| P-hydroxy benzyl benzoate | 0.18 |
| Guaiazulene (azulene 100%, 1,4-dimethyl-7-isopropyl-azulene) | 0.02 |
| | 100.00 |

I claim:

1. A skin conditioner composition comprising an effective amount of the following constituents: d-alpha tocopherol liquid; PCL wax or solid; PCL oil; fumed silica; squalane; decyl oleate; wheat germ glyceride; a subcomposition of lecithin, butyl stearate, cocoyl hydrolyzed collagen, oleyl sarcosine, sesame oil and lanolin alcohol; ppg-26 oleate perfume; p-hydroxy benzyl benzoate; guaiazulene.

2. A skin conditioner composition comprising an effective amount of the following constituents blended in the following ranges of percentage by weight:

| | |
|---|---|
| D-alpha tocopherol liquid | 45–55 |
| PCL wax or solid | 14–18 |
| PCL oil | 7–9 |
| Fumed silica | 6–8 |
| Decyl oleate | 4–6 |
| Squalane | 4–6 |
| Wheat germ glyceride | 3–4 |
| a subcomposition of lecithin, butyl stearate, cocoyl hydrolyzed collagen, oleyl sarcosine, sesame oil and lanolin alcohol | 3–4 |
| Ppg-26 oleate (polyoxy propylene ester) | 1–3 |
| Perfume | 0.20 |
| P-hydroxy benzyl benzoate | 0.18 |
| Guaiazulene (azulene 100%, 1,4-dimethyl-7-isopropyl-azulene). | 0.02 |

3. A skin conditioner composition comprising following constituents in percentage by weight:

| | |
|---|---|
| D-alpha tocopherol liquid | 50.00 |
| PCL wax or solid | 16.00 |
| PCL oil | 8 |
| Fumed silica | 7 |
| Decyl oleate | 5 |
| Squalane | 5 |
| Wheat germ glyceride | 3.60 |
| a subcomposition of lecithin, butyl stearate, cocoyl hydrolyzed collagen, oleyl sarcosine, sesame oil and lanolin alcohol | 3.00 |
| Ppg-26 oleate (polyoxy propylene ester) | 2.00 |
| Perfume | 0.20 |
| P-hydroxy benzyl benzoate | 0.18 |
| Guaiazulene (azulene 100%, 1,4-dimethyl-7-isopropyl-azulene) | 0.02 |
| | 100.00. |

* * * * *